United States Patent
Arakawa

(10) Patent No.: US 10,271,967 B2
(45) Date of Patent: Apr. 30, 2019

(54) DRIVING APPARATUS AND DRIVING METHOD THEREFOR

(71) Applicant: Seiko Epson Corporation, Tokyo (JP)

(72) Inventor: Yutaka Arakawa, Hara (JP)

(73) Assignee: Seiko Epson Corporation (JP)

( * ) Notice: Subject to any disclaimer, the term of this patent is extended or adjusted under 35 U.S.C. 154(b) by 718 days.

(21) Appl. No.: 14/851,440

(22) Filed: Sep. 11, 2015

(65) Prior Publication Data

US 2016/0074179 A1 Mar. 17, 2016

(30) Foreign Application Priority Data

Sep. 12, 2014 (JP) ................................ 2014-185853
Sep. 12, 2014 (JP) ................................ 2014-185854
Sep. 12, 2014 (JP) ................................ 2014-185856

(51) Int. Cl.
*A61F 2/70* (2006.01)
*A61F 5/01* (2006.01)

(52) U.S. Cl.
CPC .............. *A61F 2/70* (2013.01); *A61F 5/013* (2013.01); *A61F 2005/0155* (2013.01)

(58) Field of Classification Search
CPC .......... A61F 5/013; A61F 2/70; A61F 5/0118; A61H 1/0285; A61H 1/0288; A61H 2201/1635
See application file for complete search history.

(56) References Cited

U.S. PATENT DOCUMENTS

| | | | |
|---|---|---|---|
| 5,376,091 A * | 12/1994 | Hotchkiss | A61B 17/62 602/22 |
| 6,502,577 B1 * | 1/2003 | Bonutti | A61F 5/013 128/898 |
| 7,224,102 B2 * | 5/2007 | Miyazawa | H02N 2/004 310/323.02 |
| 8,579,991 B2 | 11/2013 | Puchhammer | |
| 8,668,659 B2 | 3/2014 | Kawakami | |
| 8,827,428 B2 | 9/2014 | Miyazawa et al. | |
| 8,998,831 B2 | 4/2015 | Sankai | |
| 9,820,908 B2 * | 11/2017 | Elia | A61H 1/00 |
| 2010/0245517 A1 | 9/2010 | Miyazawa et al. | |
| 2010/0249676 A1 * | 9/2010 | Kawakami | A61F 5/013 601/40 |

(Continued)

FOREIGN PATENT DOCUMENTS

CN 103078555 A 5/2013
JP 05-009894 U 2/1993

(Continued)

*Primary Examiner* — Nyca T Nguyen
(74) *Attorney, Agent, or Firm* — Harness, Dickey & Pierce, P.L.C.

(57) ABSTRACT

A driving apparatus including a base member, a first member rotatably provided on the base member, and a driver configured to rotate the first member around a rotation shaft. The driver further includes a vibrating plate including a piezoelectric body, and a driven member contacting with the vibrating plate. The driven member is configured to be driven in contact with the vibrating plate. Further, the first member is rotatable around the rotation shaft, the rotation shaft configured to be placed along an index finger metacarpal bone of a hand when the base member is placed on a back of the hand.

6 Claims, 13 Drawing Sheets

(56) References Cited

U.S. PATENT DOCUMENTS

| | | | |
|---|---|---|---|
| 2010/0305717 A1* | 12/2010 | Tong | A61H 1/0285 623/64 |
| 2010/0318009 A1* | 12/2010 | Stanley | A61F 7/007 602/14 |
| 2012/0029399 A1* | 2/2012 | Sankai | A61B 5/04888 601/40 |
| 2013/0299235 A1 | 11/2013 | Adachi et al. | |
| 2014/0198626 A1 | 7/2014 | Miyazawa et al. | |
| 2014/0243721 A1* | 8/2014 | Bryant | A61F 5/013 602/21 |

FOREIGN PATENT DOCUMENTS

| | | |
|---|---|---|
| JP | 11-253504 A | 9/1999 |
| JP | 2001-104349 A | 4/2001 |
| JP | 2002-345861 A | 12/2002 |
| JP | 2002-354649 A | 12/2002 |
| JP | 2004-056948 A | 2/2004 |
| JP | 2009-083020 A | 4/2009 |
| JP | 2009-519795 A | 5/2009 |
| JP | 2009-125887 A | 6/2009 |
| JP | 2009-201648 A | 9/2009 |
| JP | 2010-063723 A | 3/2010 |
| JP | 2010-240285 A | 10/2010 |
| JP | 2011-115248 A | 6/2011 |
| JP | 2012-152047 A | 8/2012 |
| JP | 2012-187426 A | 10/2012 |
| JP | 2012-250048 A | 12/2012 |
| JP | 2012-253990 A | 12/2012 |
| JP | 2013-240464 A | 12/2013 |
| KR | 10-2011-0032852 A | 3/2011 |

\* cited by examiner

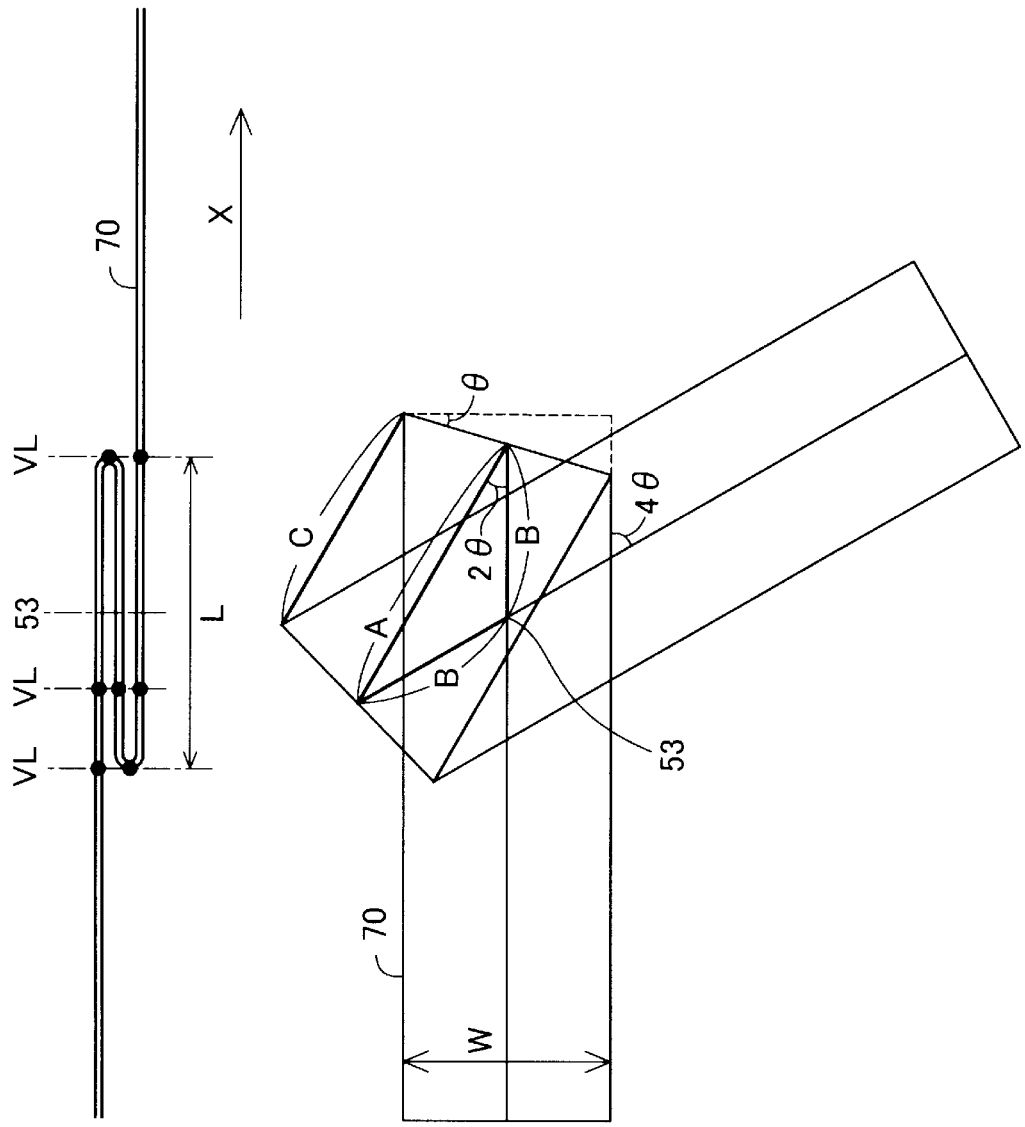

DRIVING APPARATUS AND DRIVING METHOD THEREFOR

BACKGROUND

1. Technical Field

The present invention relates to a driving apparatus and a driving method therefor.

2. Related Art

JP-A-2011-115248 discloses a wearable motion assist apparatus that assists finger motions worn on a hand by bending and stretching finger joints.

Further, regarding the technology of wiring to a joint mechanism, for example, JP-A-2009-125887 discloses that, to reduce load when a finger member of a robot hand is driven, two or more bending points are provided to a wire connected to the finger member for sagging of the wire.

However, the apparatus disclosed in JP-A-2011-115248 is adapted on the assumption of assistance for index finger motions, but thumb motions are not considered. Accordingly, a technology that enables favorable assistance of thumb motions is required. This task is not only for humans but also common to the cases of assisting motions of the joints of living bodies including animals and joints of non-living bodies including robots.

Further, in the joint mechanism disclosed in JP-A-2009-125887, there are various kinds of wiring in the joint mechanism. For example, when a flat wiring member is wired in the joint mechanism, the degree of freedom of motion of the joint mechanism may be restricted depending on its layout. This is because the flat wiring member is harder to be bent in a direction in parallel to its surface. Therefore, a technology that can suppress restriction of the motions of the joint mechanism when the flat wiring member is wired to the joint mechanism is required. This task is not only for the joint parts of the robot but also common to an apparatus of assisting motions of joints of living bodies including humans and animals and various joint mechanisms capable of bending motions.

SUMMARY

An advantage of some aspects of the invention is to solve at least a part of the problems described above, and the invention can be implemented as the following forms.

(1) An aspect of the invention provides a driving apparatus. The driving apparatus includes a base member, and a first member rotatably provided on the base member, wherein the first member is rotatable about a rotation shaft along an index finger metacarpal bone of a hand when the base member is placed on a back of the hand.

According to the driving apparatus having the configuration, the motion of the ball side of the thumb turning to the palm side may be favorably assisted by the first member.

(2) The driving apparatus according to the aspect of the invention may include a rotation unit that rotates the first member about the rotation shaft.

According to the configuration, the first member is rotated by the rotation unit, and thereby, the motion of the ball side of the thumb turning to the palm side may be favorably assisted.

(3) In the driving apparatus according to the aspect of the invention, the rotation unit may include a vibrating plate including a piezoelectric body, and a driven part driven in contact with the vibrating plate.

According to the configuration, the rotation unit may be formed to be smaller and the driving apparatus may be downsized.

(4) In the driving apparatus according to the aspect of the invention, a projecting portion may be provided on the vibrating plate, and the projecting portion may be in contact with the driven part.

According to the configuration, the vibrating plate is not in contact with the driven part, but the projecting portion is in contract with the driven part, and thereby, durability of the rotation unit may be improved.

(5) The driving apparatus according to the aspect of the invention may include an elastic member provided between the first member and the hand.

According to the configuration, rubbing of the first member by the hand may be suppressed, and the first member may be smoothly rotated about the rotation shaft.

(6) Another aspect of the invention provides a driving apparatus. The driving apparatus includes a base member that can be placed on a back of a hand, a first member that is provided on the base member and can be placed on a thumb of the hand, a second member rotatable in a first rotation direction with respect to the first member, and a rotation unit that rotates the second member in the first rotation direction with respect to the first member. Further, a distance between the base member and the second member is variable.

According to the driving apparatus having the configuration, the first member and the second member can be rotated by the rotation unit, further, the distance between the base member and the second member is adapted to be variable, and thereby, the thumb motion may be favorably assisted by the second member.

(7) In the driving apparatus according to the aspect of the invention, the first member may have a first connecting part provided in the base member and a second connecting part provided in the second member, and the first connecting part and the second connecting part move closer to and away from each other, and thereby, the distance between the base member and the second member may vary.

According to the driving apparatus having the configuration, the distance between the base member and the second member may be varied by the simple configuration.

(8) In the driving apparatus according to the aspect of the invention, the first connecting part may include a first auxiliary member provided in the base member and a second auxiliary member provided in the second connecting part rotatably in the first rotation direction with respect to the first auxiliary member.

According to the driving apparatus having the configuration, the degree of freedom of the motion of the first connecting part is improved, and thereby, the thumb motion may be more favorably assisted.

(9) The driving apparatus according to the aspect of the invention may include a rotation unit that rotates the second auxiliary member in the first rotation direction with respect to the first auxiliary member.

According to the driving apparatus having the configuration, the second auxiliary member may be rotated by the rotation unit, and thereby, the thumb motion may be more favorably assisted.

(10) In the driving apparatus according to the aspect of the invention, the first rotation direction may be a direction in which the thumb opens and closes with respect to an index finger of the hand.

According to the driving apparatus having the configuration, the thumb motion may be more favorably assisted.

(11) In the driving apparatus according to the aspect of the invention, the second member may include a third connecting part provided in the first member, a fourth connecting part provided in the third connecting part, and a fifth connecting part provided in the fourth connecting part, and the fourth connecting part and the fifth connecting part may be rotatable in a second rotation direction different from the first rotation direction with respect to the third connecting part.

According to the driving apparatus having the configuration, the degree of freedom of the motion of the driving apparatus may be improved, and thereby, the thumb motion may be more favorably assisted.

(12) In the driving apparatus according to the aspect of the invention, a rotation unit that rotates the fourth connecting part in the second rotation direction with respect to the third connecting part may be provided.

According to the driving apparatus having the configuration, the fourth connecting part may be rotated by the rotation unit, and thereby, the thumb motion may be more favorably assisted.

(13) In the driving apparatus according to the aspect of the invention, the second rotation direction may be a direction in which the thumb bends.

According to the driving apparatus having the configuration, the thumb motion may be more favorably assisted.

(14) In the driving apparatus according to the aspect of the invention, a fixing part attached to the thumb may be provided in the second member and the fixing part may be slidable along a proximal phalanx of the thumb.

According to the driving apparatus having the configuration, the thumb motion may be more favorably assisted.

(15) In the driving apparatus according to the aspect of the invention, the first member may be rotatable about a rotation shaft along an index finger metacarpal bone of the hand with respect to the base member.

According to the driving apparatus having the configuration, the motion of the ball side of the thumb turning to the palm side may be favorably assisted by the first member.

(16) The driving apparatus according to the aspect of the invention may include a rotation unit that rotates the first member about a rotation shaft along the index finger metacarpal bone of the hand with respect to the base member.

According to the driving apparatus having the configuration, the first member may be rotated by the rotation unit with respect to the base part, and thereby, the thumb motion may be more favorably assisted.

(17) In the driving apparatus according to the aspect of the invention, the respective rotation units may include vibrating plates including piezoelectric bodies and driven parts driven in contact with the vibrating plates.

According to the driving apparatus having the configuration, the respective rotation units may be made smaller, and thereby, the driving apparatus may be downsized.

(18) In the driving apparatus according to the aspect of the invention, a projecting portion may be provided on the vibrating plate, and the projecting portion may be in contact with the driven part.

According to the driving apparatus having the configuration, the vibrating plate is not in contact with the driven part, but the projecting portion is in contract with the driven part, and thereby, durability of the rotation unit may be improved.

(19) Still another aspect of the invention provides a joint mechanism. The joint mechanism includes a first member, a second member provided in the first member rotatably about a rotation shaft, and a flat wiring member. Further, the flat wiring member is bent to have parts of three or more intersection points with a virtual line in parallel to the rotation shaft.

According to the joint mechanism having the configuration, even when the first member and the second member are rotated about the rotation shaft, the flat wiring member may be allowed to follow the motion, and thus, restriction on the motion of the joint mechanism due to presence of the flat wiring member may be suppressed.

(20) In the joint mechanism according to the aspect of the invention, the flat wiring member may be fixed to at least one of the first member and the second member.

According to the joint mechanism having the configuration, unstableness of the flat wiring member may be suppressed.

(21) In the joint mechanism according to the aspect of the invention, the first member may have a first cavity part and the second member may have a second cavity part, and the flat wiring member may pass through the first cavity part and the second cavity part.

According to the joint mechanism having the configuration, the flat wiring member passes inside of the first cavity part and the second cavity part, and thereby, the joint mechanism may be downsized.

(22) In the joint mechanism according to the aspect of the invention, the flat wiring member may be a flexible substrate.

According to the joint mechanism having the configuration, it is not necessary to form the flat wiring member using a special material, and therefore, the manufacturing cost of the joint mechanism may be reduced.

(23) In the joint mechanism according to the aspect of the invention, in the case where the flat wiring member has intersection parts at three points with a virtual line in parallel to the rotation shaft, suppose that a width of the flat wiring member is W, and a distance between the two parts at two points at which the virtual line intersects with the flat wiring member in a direction in which the first member and the second member extend when the first member and the second member are not rotated is L, the second member may be rotatable with respect to the first member to an angle four times θ that satisfies the following expression (1).

$$2L \cos θ/(\cos 2θ+1) - W \tan θ > 0 \qquad (1)$$

According to the joint mechanism having the configuration, the range of rotation angle of the joint mechanism is specified by the expression (1). Accordingly, the joint mechanism may be easily designed.

(24) Yet another aspect of the invention provides a driving apparatus. The driving apparatus includes the joint mechanism having any one of the above described configurations and a rotation unit that rotates the first member and the second member about the rotation shaft.

According to the driving apparatus having the configuration, the flat wiring member is bent in advance as described above, and thereby, load on the rotation unit may be suppressed.

The invention can be implemented in various other configurations than the configurations as the above described joint mechanism and driving apparatus. For example, the invention can be implemented in configurations of a driving method for the joint mechanism or driving mechanism, a joint driving apparatus that assists joint motions, etc.

BRIEF DESCRIPTION OF THE DRAWINGS

The invention will be described with reference to the accompanying drawings, wherein like numbers reference like elements.

FIGS. 6A and 6B are diagrams for explanation of a range of rotation angle of the joint mechanism.

DESCRIPTION OF EXEMPLARY EMBODIMENTS

A. Configuration of Driving Apparatus

Figure 1:
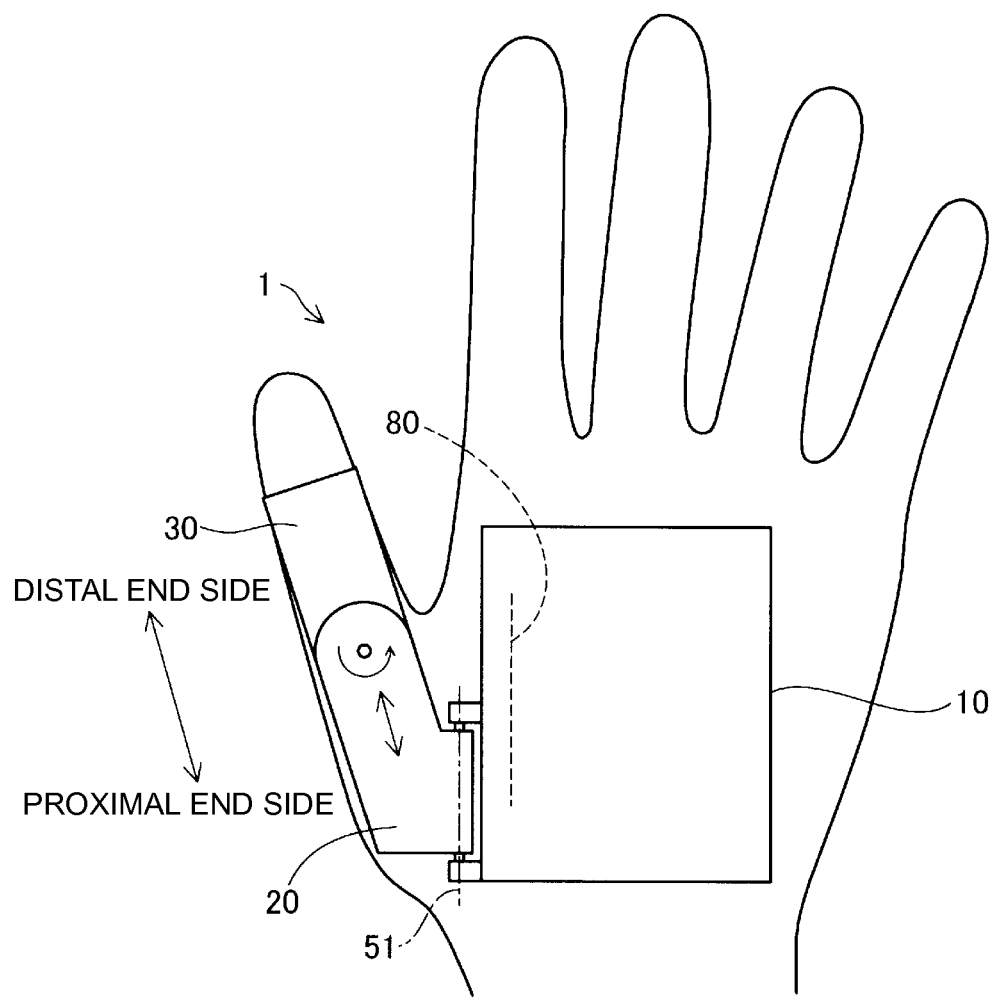
FIG. 1 is a schematic diagram showing an overall configuration of a driving apparatus as one embodiment of the invention.

FIG. 1 is a schematic diagram showing an overall configuration of a driving apparatus 1 as one embodiment of the invention. For example, the driving apparatus 1 is attached to a hand of a person having difficulty in bending and stretching of a finger due to an accident or disease, a person having a weaker grip, a person having less strength with age and used for assisting finger motions.

The driving apparatus 1 of the embodiment is particularly used for assisting motions of a thumb of a hand. As below, when the driving apparatus 1 is attached to a hand as an attached part, the tip side of the thumb is referred to as "distal end side" or "front side" and the base side of the thumb (the part around the third joint) is referred to as "proximal end side" or "rear side". Further, in the specification, "finger" of a hand refers to apart from a finger tip to the third joint regardless of which finger. Furthermore, "hand" includes "fingers".

The driving apparatus 1 includes a base member 10, a first member 20, and a second member 30.

The base member 10 is a member placed on the back side of a hand. The base member 10 has an outer shape in a flat block, and is, for example, attached to the hand using an arbitrary fastening such as a band or hook.

The first member 20 is provided on the base member 10 rotatably about a first rotation shaft 51 along an index finger metacarpal bone 80 of the hand. The first member 20 is placed from the vicinity of the third joint to the vicinity of the second joint on the back side of the thumb. The second member 30 is a member rotatable relative to the first member 20. The distal end part of the second member 30 is fixed between the first joint to the second joint on the back side of the thumb. As will be described later, the driving apparatus 1 is adapted so that the distance between the base member 10 and the second member 30 may be varied. Note that the first rotation shaft 51 about which the first member 20 rotates is a shaft in a different direction from that of an axis about which the index finger of the hand rotates.

Figure 2:
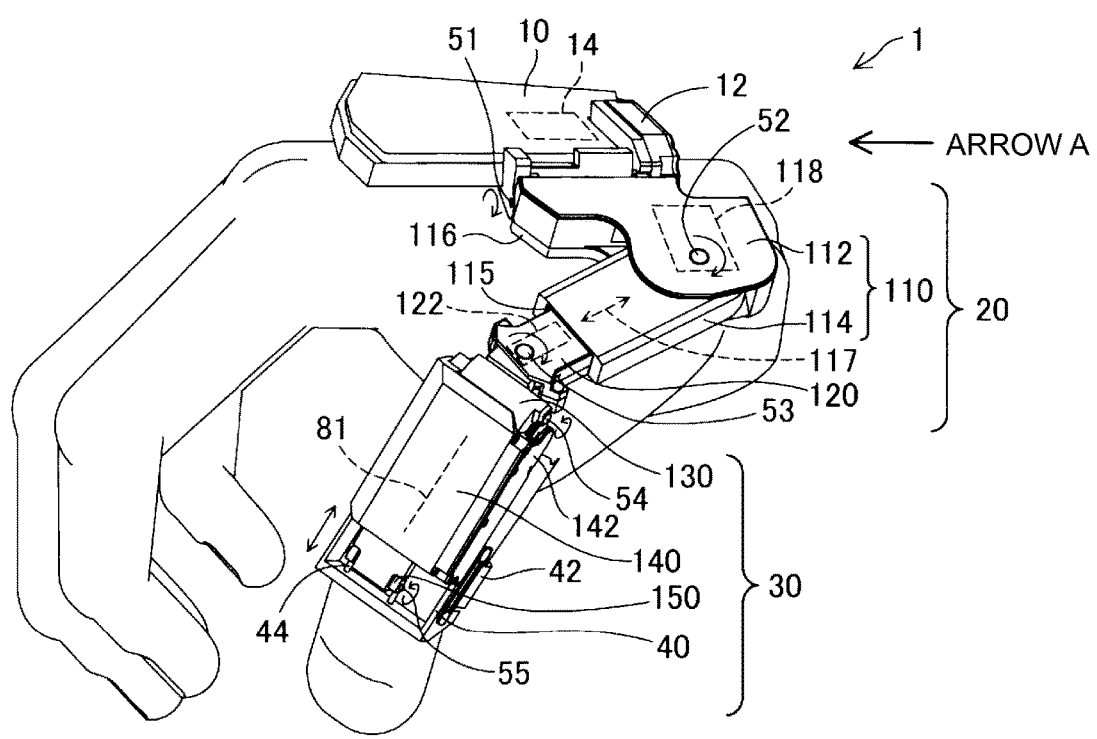
FIG. 2 shows a detailed configuration of the driving apparatus.

FIG. 2 shows a detailed configuration of the driving apparatus 1. The base member 10 includes the first rotation shaft 51, a first rotation unit 12, and a control unit 14.

The first member 20 is connected to the first rotation shaft 51. The first rotation unit 12 drives the first rotation shaft 51 to relatively rotate the first member 20 about the first rotation shaft 51. The detailed configuration of the first rotation unit 12 will be described later.

The control unit 14 includes a circuit for assisting the thumb motion by controlling the first rotation unit 12 and a second rotation unit 118, a third rotation unit 122, and a fourth rotation unit 142, which will be described later. The control unit 14 may be provided in another part than the base member 10.

The first member 20 includes a first connecting part 110 and a second connecting part 120. The first connecting part 110 includes a first auxiliary member 112 and a second auxiliary member 114.

The first auxiliary member 112 is a member rotatable about the first rotation shaft 51 of the base member 10. The first auxiliary member 112 includes an elastic member 116, the second rotation unit 118, and a second rotation shaft 52. The elastic member 116 is provided between the first auxiliary member 112 and the back of the hand. As a material for the elastic member 116, e.g., elastic rubber, a sponge, or a spring may be used. Note that the elastic member 116 may be omitted.

The second rotation unit 118 is provided within the first auxiliary member 112 and drives the second rotation shaft 52. The second rotation shaft 52 is placed near the third joint of the thumb when the driving apparatus 1 is attached to the hand. The second rotation shaft 52 extends along an axis about which the thumb opens and closes around the third joint with respect to the index finger. The proximal end part of the second auxiliary member 114 is connected to the second rotation shaft 52 rotatably about the second rotation shaft 52. Accordingly, the second rotation unit 118 may drive the second auxiliary member 114 in a direction in which the thumb opens and closes with respect to the index finger (first rotation direction). Note that the second rotation unit 118 may be provided outside of the first auxiliary member 112.

The second auxiliary member 114 has a nearly rectangular parallelepiped shape. The second auxiliary member 114 includes an opening part 115 in its distal end surface. The proximal end part of the second connecting part 120 is inserted into the opening part 115. A first sliding mechanism 117 for slidingly moving the second connecting part 120 in the distal and proximal directions is provided within the second auxiliary member 114. In the embodiment, the second connecting part 120 slidingly moves with respect to the second auxiliary member 114 by the first sliding mechanism 117, and thereby, the distance between the base member 10 and the second member 30 varies.

The second connecting part 120 has a nearly rectangular parallelepiped shape. The second connecting part 120 includes the third rotation unit 122 and a third rotation shaft 53. The third rotation unit 122 is provided within the second connecting part 120 and drives the third rotation shaft 53. The third rotation shaft 53 is placed near the second joint of the thumb when the driving apparatus 1 is attached to the hand. The third rotation shaft 53 is in parallel to the second rotation shaft 52 provided in the first connecting part 110. The proximal end part of the second member 30 is connected to the second connecting part 120 rotatably about the third rotation shaft 53. Accordingly, the third rotation unit 122 may drive the second member 30 in the direction in which the thumb opens and closes with respect to the index finger (first rotation direction).

The second member 30 includes a third connecting part 130, a fourth connecting part 140, and a fifth connecting part 150. A fixing part 40 is connected to the distal end part of the second member 30.

The third connecting part 130 has a shorter length in the distal and proximal directions than the second connecting part 120 and the fourth connecting part 140. The proximal end part of the third connecting part 130 is connected to the second connecting part 120 rotatably about the third rotation shaft 53. A fourth rotation shaft 54 is provided in the distal end part of the third connecting part 130. The fourth rotation shaft 54 is a shaft perpendicular to the second rotation shaft 52 and the third rotation shaft 53.

The fourth connecting part 140 has a nearly rectangular parallelepiped shape. The proximal end part of the fourth connecting part 140 is connected to the third connecting part 130 rotatably about the fourth rotation shaft 54. The fourth connecting part 140 includes the fourth rotation unit 142 and a fifth rotation shaft 55. The fourth rotation unit 142 drives the fourth rotation shaft 54 provided in the third connecting part 130. The fourth rotation shaft 54 is a shaft perpendicular to the second rotation shaft 52 and the third rotation shaft 53, and thereby, the fourth rotation unit 142 may drive the fourth connecting part 140 in a direction in which the thumb bends (second rotation direction). The fifth rotation shaft 55 is a shaft in parallel to the fourth rotation shaft 54 and provided in the distal end part of the fourth connecting part 140.

The fifth connecting part 150 is connected to the distal end part of the fourth connecting part 140 rotatably about the fifth rotation shaft 55 (i.e., in the second rotation direction). Further, the fifth connecting part 150 is connected to a second sliding mechanism 44 provided on the upper surface side of the fixing part 40. The second sliding mechanism 44 can slidably move the fifth connecting part 150 relatively along a proximal phalanx 81 of the thumb. That is, the fifth connecting part 150 is movable with respect to the fourth connecting part 140 and slidable in the distal and proximal directions with respect to the fixing part 40.

The fixing part 40 includes an attachment band 42 on the lower surface side. The attachment band 42 is wrapped between the first joint and the second joint of the thumb, and thereby, the fixing part 40 is attached to the thumb. The attachment band 42 is formed using e.g. various rubber materials including silicone rubber.

As described above, the driving apparatus 1 is formed by sequential connection of the base member 10, the first connecting part 110 (the first auxiliary member 112 and the second auxiliary member 114), the second connecting part 120, the third connecting part 130, the fourth connecting part 140, the fifth connecting part 150, and the fixing part 40 from the back of the hand toward the distal end side of the thumb. As below, these members may be referred to as "movable members". The respective movable members may be formed using e.g. various resin materials including polyethylene or various metal materials including aluminum.

B. Overall Configuration of Rotation Unit

Figure 3:
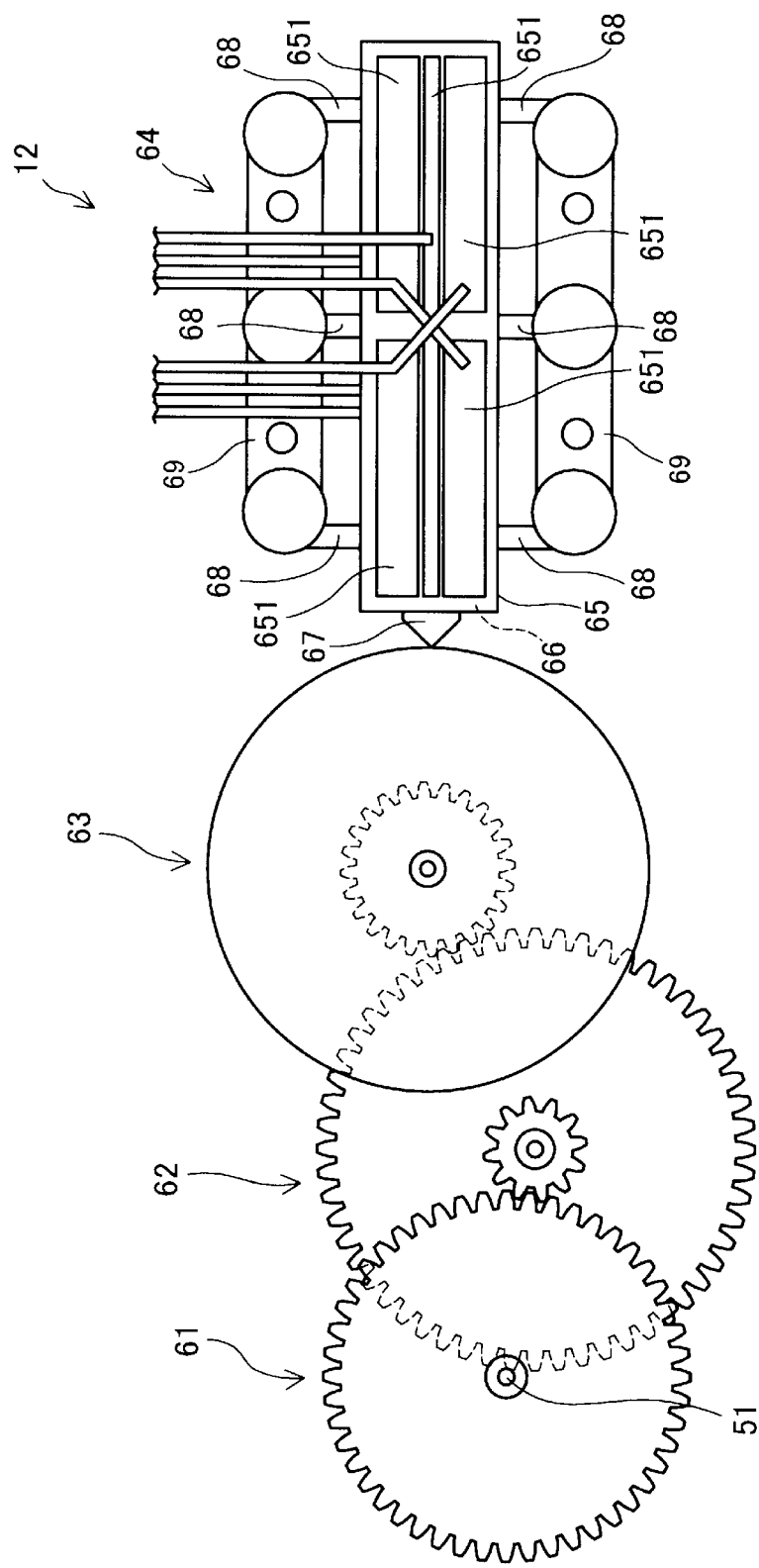
FIG. 3 is an explanatory diagram showing an overall configuration of a first rotation unit.

FIG. 3 is an explanatory diagram showing an overall configuration of the first rotation unit 12. The second rotation unit 118, the third rotation unit 122, and the fourth rotation unit 142 have the same configuration as the first rotation unit 12, and the explanation of the configurations of these rotation units will be omitted.

The first rotation unit 12 has a first rotor 61 coaxially coupled to the first rotation shaft 51, a second rotor 62 that rotates the first rotor 61, a third rotor 63 that rotates the second rotor 62, and a piezoelectric drive device 64 that rotates the third rotor 63. The first rotor 61, the second rotor 62, and the third rotor 63 are formed as a gear train (driven part). When the third rotor 63 rotates by the piezoelectric drive device 64, the first rotor 61 rotates in response thereto. Then, the rotation shaft (first rotation shaft 51) coupled to the first rotor 61 rotates in response to the rotation of the first rotor 61, and the first connecting part 110 rotates with respect to the base member 10 in response thereto. Note that the number of rotors and the gear ratios of the respective rotors can be arbitrarily changed in response to the rotation directions of the shafts to drive, required torque, etc.

The piezoelectric drive device 64 includes a vibrating plate 66 on which piezoelectric bodies (piezoelectric elements) 651 are provided. More specifically, vibrators 65 having the five piezoelectric bodies 651 are respectively bonded to the front surface and the rear surface of the vibrating plate 66, and thereby, the piezoelectric drive device 64 is formed.

Each of the five piezoelectric bodies 651 forming the vibrator 65 has a piezoelectric body and a first electrode and a second electrode sandwiching the piezoelectric body (not shown). Note that one of the first electrode and the second electrode may be a common electrode. These piezoelectric bodies 651 are electrically connected to the control unit 14 shown in FIG. 2. At least one piezoelectric body 651 contained in the vibrator 65 is necessary, and various other numbers and arrangements of the piezoelectric bodies 651 may be employed. Further, the vibrator 65 may be provided only on one surface of the two surfaces (the front side surface and the rear side surface) of the vibrating plate 66.

A projecting portion 67 is provided in the end part of the piezoelectric drive device 64 (vibrating plate 66). It is preferable that the projecting portion 67 is formed using a material having durability including ceramics (e.g. $Al_2O_3$). A plurality of supporting portions 68 for supporting the piezoelectric drive device 64 are provided on both side surfaces of the piezoelectric drive device 64 in positions corresponding to nodes of the vibration of the piezoelectric drive device 64. These supporting portions 68 are integrally formed with the vibrating plate 66. Note that it is preferable that the plurality of supporting portions 68 projecting from the same side surfaces of the vibrating plate 66 are coupled via coupling plates 69.

Figure 4A:
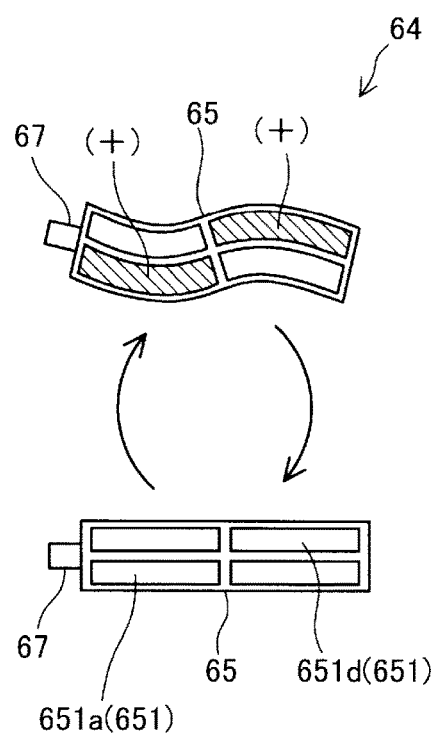
FIGS. 4A and 4B are explanatory diagrams showing an operation principle of a piezoelectric drive device.
Figure 4B:
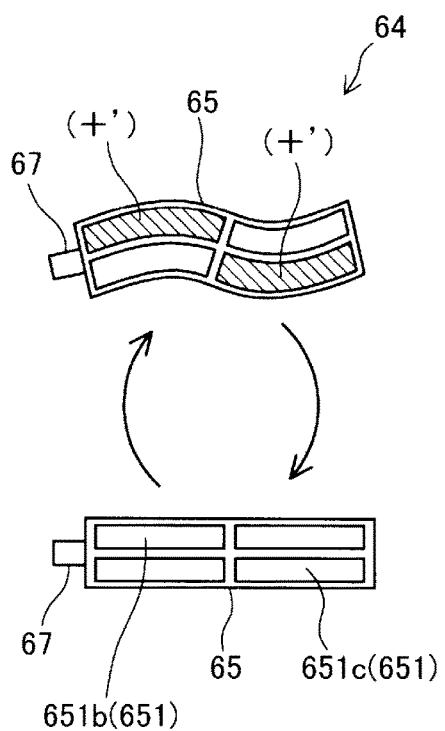

FIGS. 4A and 4B are explanatory diagrams showing an operation principle of the piezoelectric drive device 64. When voltages are applied to the piezoelectric bodies 651 of each piezoelectric drive device 64 in a constant cycle, the projecting portion 67 of the piezoelectric drive device 64 makes an expanding and contracting motion (reciprocating motion) or elliptic motion, and thereby, the piezoelectric drive device 64 operates.

That is, as shown in FIG. 4A, with two piezoelectric bodies 651a, 651d diagonally located to each other as one pair, when a voltage at a specific frequency is applied thereto, the piezoelectric drive device 64 is bent and deformed into a meandering shape (S-shape), and the tip end of the projecting portion 67 makes a reciprocating motion in specific directions or elliptic motion. As a result, the third rotor 63 (FIG. 3) in contact with the projecting portion 67 rotates in a predetermined direction. Further, as shown in FIG. 4B, when a voltage at a specific frequency is applied to the other pair of piezoelectric bodies 651b, 651c, the third rotor 63 rotates in the opposite direction.

Note that the motions of the piezoelectric drive device 64 and the vibrator 65 are disclosed in JP-A-2004-320979 or its counterpart U.S. Pat. No. 7,224,102 and the disclosure is incorporated herein by reference.

C. Structure of Joint Mechanism

Figure 5A:
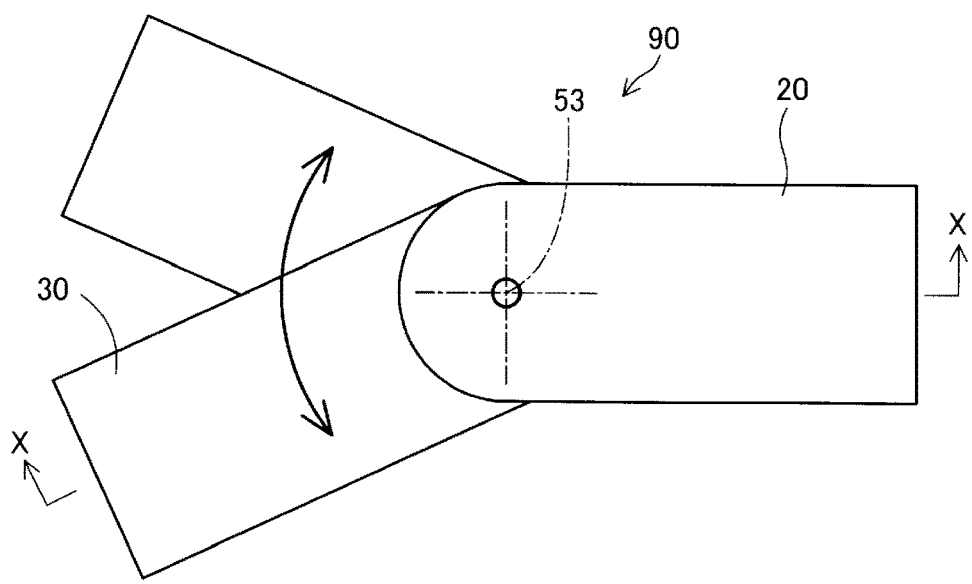
FIGS. 5A to 5C show a structure of a joint mechanism provided in the driving apparatus.
Figure 5B:
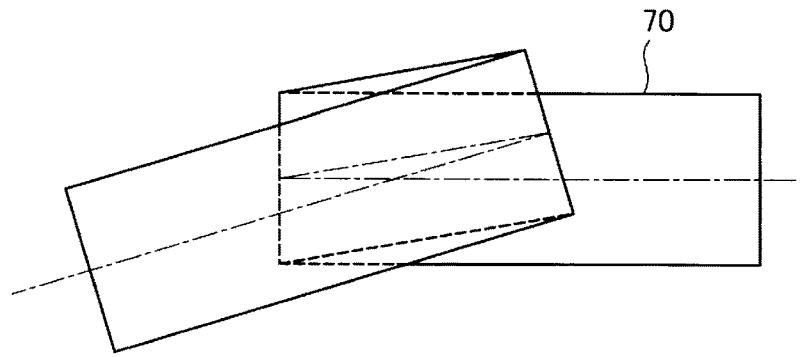
Figure 5C:
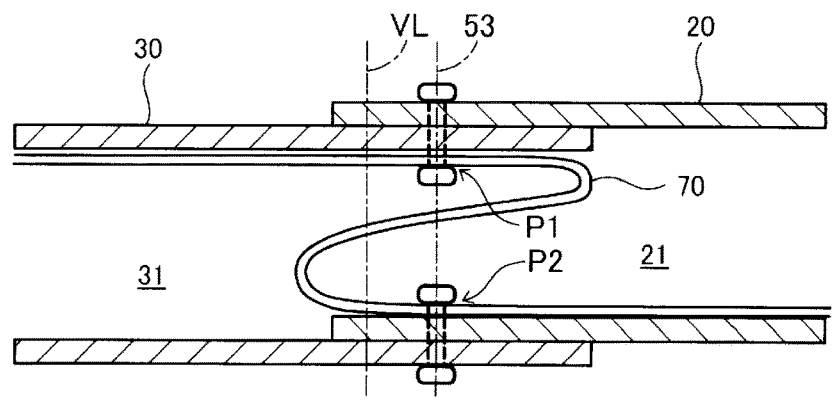

FIGS. 5A to 5C show a structure of a joint mechanism 90 provided in the driving apparatus 1. FIGS. 5A to 5C show the structure of the joint mechanism 90 in which the first member 20 and the second member 30 are connected by the third rotation shaft 53.

From the base member 10 to the fourth connecting part 140 (or fixing part 40) of the driving apparatus 1, a flat wiring member 70 for electrically connecting the respective rotation units to the control unit 14 is inserted inside. Accordingly, the flat wiring member 70 is also placed within the joint mechanism 90. The flat wiring member 70 is a bendable wiring member having a flat shape.

The flat wiring member 70 of the embodiment is formed by a flexible substrate. The flat wiring member 70 may have a flat or uneven surface as long as its shape is flat as a whole. As the flat wiring member 70, not only the flexible substrate but also, e.g., a flat cable in which a plurality of covered wires are arranged and fused, a ribbon-shaped flexible flat cable in which a plurality of flat conductors are arranged and covered, or the like may be employed.

FIG. 5A schematically shows a planar structure of the joint mechanism 90. Further, FIG. 5B shows a state of the flat wiring member 70 placed within the joint mechanism 90. Furthermore, FIG. 5C schematically shows a section along X-X of FIG. 5A. Note that, in FIG. 5C, the third rotation unit 122 that rotates the third rotation shaft 53 is not shown.

As shown in FIG. 5C, a first cavity part 21 is provided inside of the first member 20 and a second cavity part 31 is provided inside of the second member 30. The flat wiring member 70 is provided within the joint mechanism 90 so as to pass through the first cavity part 21 and the second cavity part 31 along the first member 20 and the second member 30.

In the embodiment, the flat wiring member 70 is fixed to the first member 20 and the second member 30 in an upper position P1 and a lower position P2 on the third rotation shaft 53. Note that the flat wiring member 70 may be fixed to one of the first member 20 and the second member 30.

The flat wiring member 70 is bent in advance so as to intersect with a virtual line VL in parallel to the third rotation shaft 53 at three points around the third rotation shaft 53. That is, the flat wiring member 70 is bent in advance in Z-fold to the degree without fold lines near the third rotation shaft 53 of the joint mechanism 90. The flat wiring member 70 is bent as described above, and thereby, the flat wiring member 70 may be easily bent with respect to the shaft perpendicular to its surface (the third rotation shaft 53) at the center. Accordingly, the first member 20 and the second member 30 forming the joint mechanism 90 may be rotated smoothly about the third rotation shaft 53.

FIGS. 5A to 5C show the state in which the flat wiring member 70 is placed within the joint mechanism 90 having the third rotation shaft 53. Also, the flat wiring member 70 is bent in advance as shown in FIG. 5C and placed within the joint mechanism having the second rotation shaft 52 as the shaft in parallel to the third rotation shaft 53 (the joint mechanism including the first auxiliary member 112 and the second auxiliary member 114).

FIGS. 6A and 6B are diagrams for explanation of a range of rotation angle of the joint mechanism 90. The range of rotation angle of the joint mechanism 90 is determined depending on the range of rotation angle of the flat wiring member 70. Accordingly, as below, the range of rotation angle of the joint mechanism 90 as the range of rotation angle of the flat wiring member 70 will be explained. FIG. 6A is a side view of the flat wiring member 70 when the first member 20 and the second member 30 are not rotated, and FIG. 6B is a plan view of the flat wiring member 70 when the first member 20 and the second member 30 are rotated. Note that, in FIG. 6A, the parts in which the flat wiring member 70 and the virtual lines VL intersect are shown by black circles.

When the flat wiring member 70 is placed within the first member 20 and the second member 30, the angle to which the second member 30 is rotatable relative to the first member 20 is specified as follows.

In the case where the flat wiring member 70 has intersection parts at three points with the virtual line VL in parallel to the third rotation shaft 53 (see FIG. 6A) and the flat wiring member 70 is fixed to the first member 20 and the second member 30 as shown in FIG. 5C, suppose that the width of the flat wiring member 70 is W as shown in FIG. 6B, and the distance between the positions at two points at which the virtual line VL intersects with the flat wiring member 70 in a direction X in which the first member 20 and the second member 30 extend when the first member 20 and the second member 30 are not rotated is L as shown in FIG. 6A, the second member 30 is rotatable relative to the first member 20 to an angle (4θ) four times θ that satisfies the following expression (1).

$$2L \cos \theta/(\cos 2\theta+1) - W \tan \theta > 0 \quad (1)$$

The range of rotation angle is specified by the expression (1) on the following grounds. First, a length A and a length B shown in FIG. 6B constantly satisfy the relationship of the following expression (2) regardless of the rotation angle of the first member 20. The length A is a length of the center line along the length direction of the flat wiring member 70 in a region in which the flat wiring member 70 is bent. The length B is a distance from the end of the center line to the third rotation shaft 53.

$$A + 2B = 2L \quad (2)$$

Then, the length A may be expressed by the following expression (3) from FIG. 6B.

$$A = 2B \cos 2\theta \quad (3)$$

By substitution of the expression (3) in the expression (2), the following expression is given.

$$2B \cos 2\theta + 2B = 2L$$

Therefore, the length B of the expression (2) is expressed as follows.

$$B = L/(\cos 2\theta + 1)$$

By substitution of the length B in the expression (2), the following expression is given.

$$A + 2L/(\cos 2\theta + 1) = 2L$$

Therefore, the length A can be expressed by the following expression (4).

$$A = 2L \cos 2\theta/(\cos 2\theta + 1) \quad (4)$$

Then, the shortest length C of the flat wiring member 70 in the region in which the flat wiring member 70 is folded may be expressed by the following expression (5) using the angle θ shown in FIG. 6B.

$$C = A - W \tan \theta \quad (5)$$

When the first member 20 rotates, it is necessary that C is larger than zero, and the expression (5) is expressed by the following expression (6).

$$A - W \tan \theta > 0 \quad (6)$$

By substitution of the length A expressed by the expression (4) in the expression (6), the following expression is obtained and the above described expression (1) is derived.

$$2L \cos 2\theta / (\cos 2\theta + 1) - W \tan \theta > 0$$

As described above, if the width W of the flat wiring member 70 and the distance L between the two positions in which the virtual lines VL intersect with the flat wiring member 70 at two points are determined, the range of rotation angle of the joint mechanism 90 is determined by the above described expression (1).

Note that, in the embodiment, the flat wiring member 70 is fixed to the first member 20 and the second member 30, however, it may be possible that the flat wiring member 70 is not fixed within the first member 20 and the second member 30. Further, in the embodiment, the flat wiring member 70 is provided inside of the joint mechanism 90, however, the flat wiring member 70 may be provided outside of the joint mechanism 90. Furthermore, in FIG. 5C, the example in which the flat wiring member 70 is bent to intersect with the virtual line VL in parallel to the third rotation shaft 53 at three points is shown, however, the flat wiring member 70 may be bent to intersect with the virtual line VL at four or more points (preferably, four or more points and an odd number of points).

D. Advantages of Driving Apparatus

Figure 7:
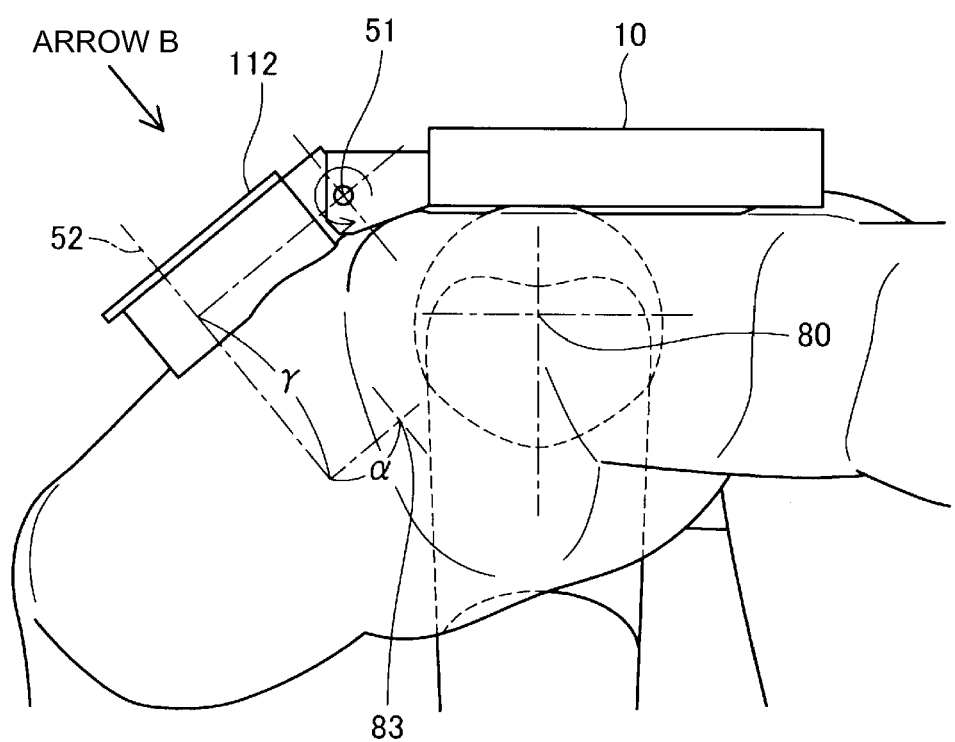
FIG. 7 is a view as seen in a direction of an arrow A in FIG. 2.
Figure 8:
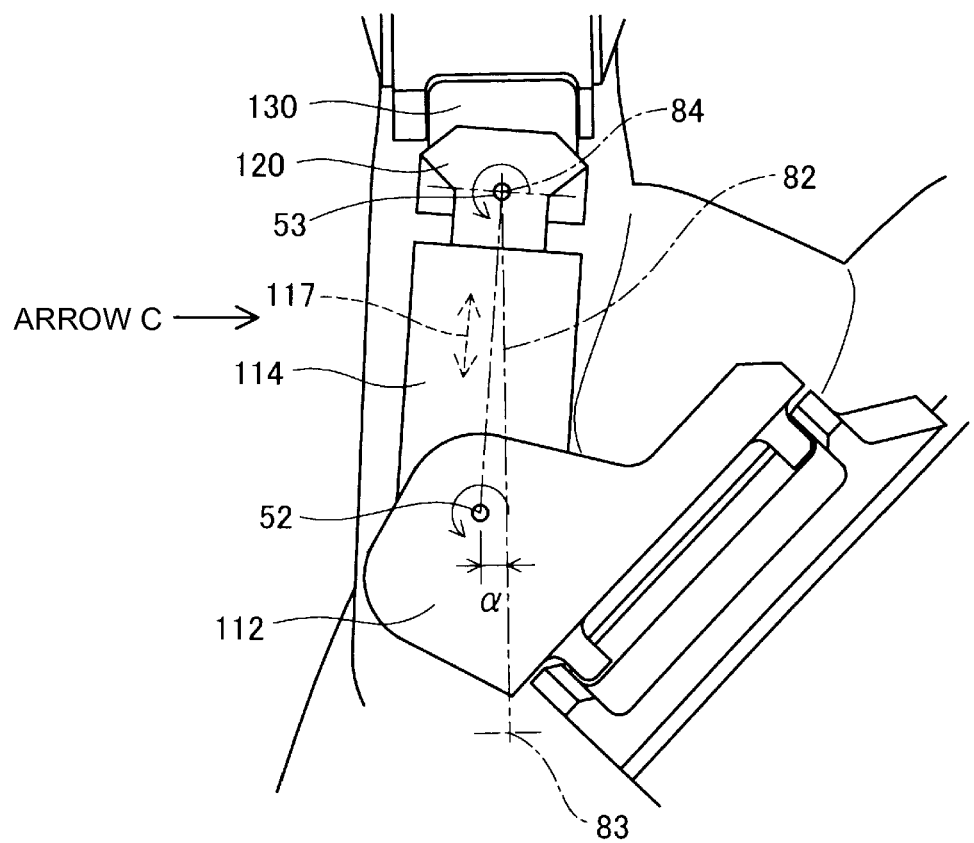
FIG. 8 is a view as seen in a direction of an arrow B in FIG. 7.
Figure 9:
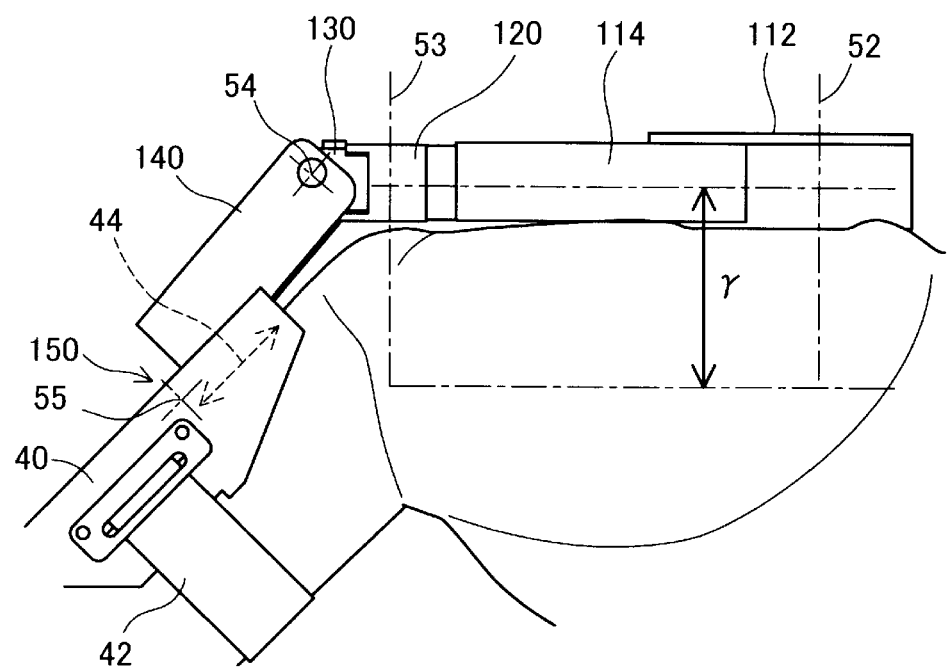
FIG. 9 is a view as seen in a direction of an arrow C in FIG. 8.

FIG. 7 is a view as seen in a direction of an arrow A in FIG. 2. FIG. 8 is a view as seen in a direction of an arrow B in FIG. 7. FIG. 9 is a view as seen in a direction of an arrow C in FIG. 8.

As shown in FIG. 7, when the driving apparatus 1 is attached to the hand, the base member 10 is placed on the back of the hand and the first rotation shaft 51 is placed along the index finger metacarpal bone 80. Accordingly, the first auxiliary member 112 connected to the first rotation shaft 51 is kept in parallel to the back side of the base of the thumb. However, even when the first rotation shaft 51 is placed along the index finger metacarpal bone 80, the first rotation shaft 51 and the index finger metacarpal bone 80 are not in the same position, and thereby, when the first auxiliary member 112 rotates about the first rotation shaft 51, a height γ from a third joint 83 of the thumb to the first auxiliary member 112 (see FIGS. 7 and 9) and a distance α from a thumb metacarpal bone 82 connecting a second joint 84 and the third joint 83 of the thumb to the second rotation shaft 52 (see FIGS. 7 and 8) change according to the motion of the thumb.

On the other hand, in the driving apparatus 1 of the embodiment, even when the distance α varies in response to the motion of the thumb, as shown in FIG. 8, the second auxiliary member 114 rotates about the second rotation shaft 52, the third connecting part 130 rotates about the third rotation shaft 53, and the second connecting part 120 slides by the first sliding mechanism 117, and thereby, they may appropriately follow the motion.

Further, in the driving apparatus 1 of the embodiment, even when the height γ varies in response to the motion of the thumb, as shown in FIG. 9, the fourth connecting part 140 rotates about the fourth rotation shaft 54, the fixing part 40 rotates about the fifth rotation shaft 55, and further the fixing part 40 and the fifth connecting part 150 slide by the second sliding mechanism 44, and thereby, they may appropriately follow the motion.

Furthermore, in the embodiment, when the respective movable members move as described above, the first rotation unit 12 drives the first rotation shaft 51, the fourth rotation unit 142 drives the fourth rotation shaft 54, and thereby, the bending motion of the thumb may be assisted. Moreover, the second rotation unit 118 drives the second rotation shaft 52, the third rotation unit 122 drives the third rotation shaft 53, and thereby, the opening and closing motion of the thumb may be assisted. That is, even when the height γ and the distance α vary in response to the motion of the thumb, the driving apparatus 1 of the embodiment may allow the respective movable members to follow the motion and appropriately assist the motion of the thumb by the respective rotation units. Accordingly, the thumb motion at the higher degree of freedom may be assisted without load on the joints of the thumb.

In addition, according to the embodiment, the following advantages may be obtained.

In the embodiment, the first member 20 is provided on the base member 10 placed on the back of the hand rotatably about the first rotation shaft 51 along the index finger metacarpal bone 80 of the hand. Accordingly, the motion of the ball side of the thumb turning to the palm side may be favorably assisted by the first member 20.

Further, the driving apparatus 1 of the embodiment includes the first rotation unit 12 that rotates the first member 20 about the first rotation shaft 51. Accordingly, the first member 20 may be actively rotated, and consequently, the motion of the ball side of the thumb turning to the palm side may be more favorably assisted.

Furthermore, in the embodiment, the respective rotation units include the piezoelectric bodies 651 and the vibrating plates 66, and thereby, the rotation units may be made smaller. Accordingly, the driving apparatus 1 may be downsized. In the embodiment, the vibrating plate is not directly contact with the driven part (gear train), but the projection portion 67 provided on the vibrating plate 66 is in contact with the driven part, and thereby, durability of the rotation unit may be improved.

Further, in the embodiment, the elastic member 116 is provided between the first member 20 and the hand, and thereby, rubbing of the first member 20 by the hand may be suppressed. Accordingly, the first member 20 may be smoothly rotated about the first rotation shaft 51.

In the driving apparatus 1 of the embodiment, the first member 20 and the second member 30 are rotated in the first rotation direction by the third rotation unit 122, and further, the distance between the base member 10 and the second member 30 is varied. Accordingly, the thumb motion may be favorably assisted by the second member 30. Further, in the embodiment, the first rotation direction is the direction in which the thumb of the hand opens and closes with respect to the index finger, and the thumb motion may be more favorably assisted.

In the embodiment, the first connecting part 110 and the second connecting part 120 provided in the first member 20 move closer to and away from each other, and thereby, the distance between the base member 10 and the second member 30 varies. Accordingly, the distance between the base member 10 and the second member 30 may be varied by the simple configuration. Further, according to the configuration, the first member 20 may be downsized.

Further, in the embodiment, the first connecting part 110 forming the first member 20 includes the first auxiliary member 112 and the second auxiliary member 114 rotatable relative to each other. Accordingly, the degree of freedom of the motion of the first connecting part 110 is higher and the thumb motion may be more favorably assisted.

The driving apparatus 1 of the embodiment includes the second rotation unit 118 that rotates the second auxiliary member 114 relative to the first auxiliary member 112. Accordingly, the second auxiliary member 114 may be actively rotated relative to the first auxiliary member 112, and consequently, the thumb motion may be more favorably assisted.

In the embodiment, the second member 30 includes the third connecting part 130, the fourth connecting part 140, and the fifth connecting part 150, and the fourth connecting part 140 and the fifth connecting part 150 are rotatable in the second rotation direction different from the first rotation direction with respect to the third connecting part 130. Accordingly, the degree of freedom of the motion of the driving apparatus 1 is higher and the thumb motion may be more favorably assisted.

The driving apparatus 1 of the embodiment includes the fourth rotation unit 142 that rotates the fourth connecting part 140 in the second rotation direction relative to the third connecting part 130. Accordingly, the fourth connecting part 140 may be actively rotated with respect to the third connecting part 130, and consequently, the thumb motion may be more favorably assisted. Further, in the embodiment, the second rotation direction is the direction in which the thumb bends, and the thumb motion may be more favorably assisted.

In the embodiment, the fixing part 40 attached to the thumb is provided in the second member 30 and the fixing part 40 is relatively slidable along the proximal phalanx 81 of the thumb. Therefore, the thumb motion may be more favorably assisted.

Further, in the joint mechanism 90 of the embodiment, the flat wiring member 70 is provided along the first member 20 and the second member 30, and the flat wiring member 70 is bent to have parts at three or more intersection points with the virtual line VL in parallel to the third rotation shaft 53. Accordingly, even when the first member 20 and the second member 30 are rotated about the third rotation shaft 53, the flat wiring member 70 may be allowed to follow the motion, and thus, restriction on the motion of the joint mechanism 90 due to presence of the flat wiring member 70 may be suppressed.

In the embodiment, the flat wiring member 70 is fixed to at least one of the first member 20 and the second member 30, and thereby, unstableness with respect to the joint mechanism 90 may be suppressed.

Further, in the embodiment, the first member 20 has the first cavity part 21 and the second member 30 has the second cavity part 31. The flat wiring member 70 passes through the first cavity part 21 and the second cavity part 31. Accordingly, the joint mechanism 90 may be downsized.

In the embodiment, the flat wiring member 70 is formed by the flexible substrate. Accordingly, it is not necessary to form the flat wiring member using a special material. Therefore, the manufacturing cost of the joint mechanism 90 may be reduced.

Further, in the embodiment, the range of rotation angle of the joint mechanism 90 may be specified by the above described expression (1). Accordingly, the joint mechanism 90 may be easily designed.

In the embodiment, the first member 20 and the second member 30 in which the flat wiring member 70 is provided are rotated by the third rotation unit 122 and, in the embodiment, the flat wiring member 70 is bent in advance as described above, and thus, the load on the third rotation unit 122 may be suppressed.

E. Modified Examples

First and Second Modified Examples

Figure 10:
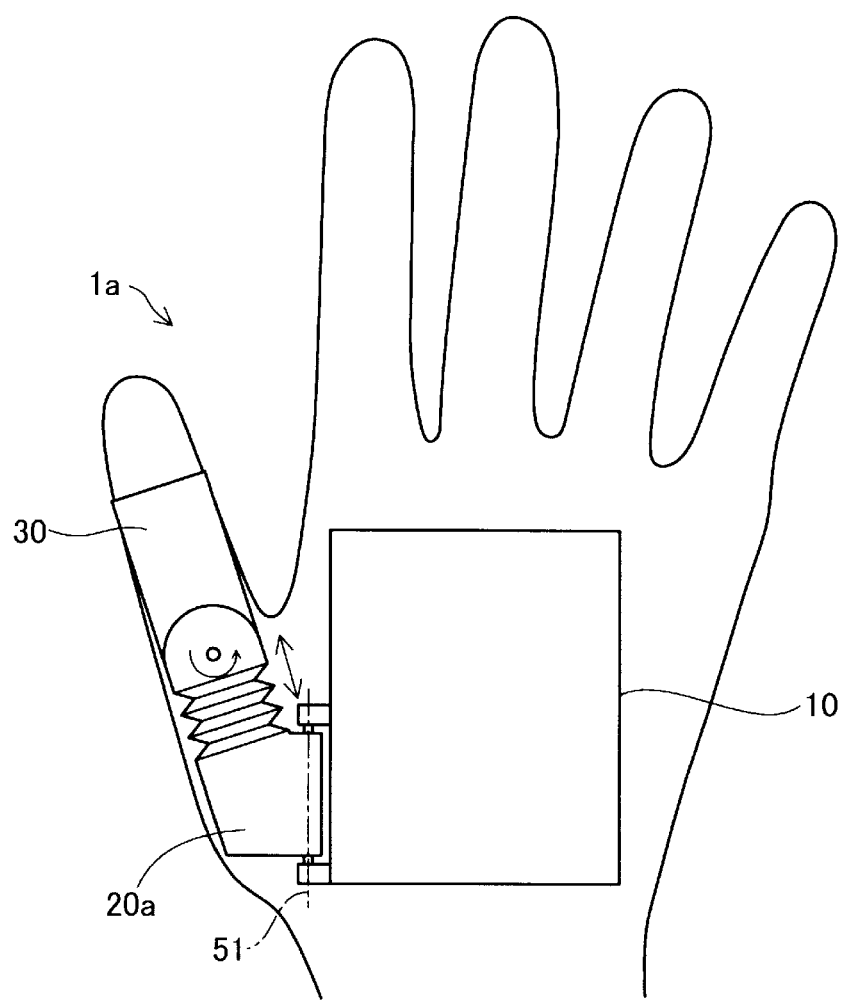
FIG. 10 shows a first modified example of the driving apparatus.
Figure 11:
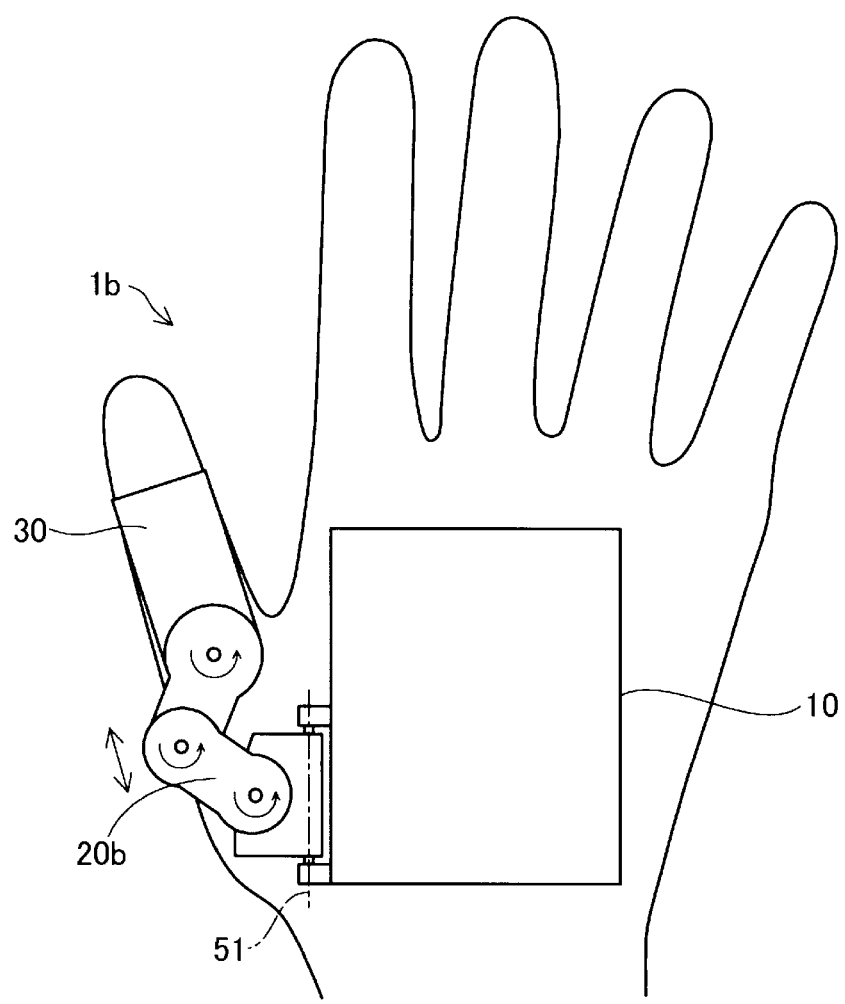
FIG. 11 shows a second modified example of the driving apparatus.

FIG. 10 shows a first modified example of the driving apparatus. FIG. 11 shows a second modified example of the driving apparatus. In the driving apparatus 1 of the above described embodiment, the second connecting part 120 and the first connecting part 110 are extended and retracted by the first sliding mechanism 117 provided in the first member 20, and thereby, the distance between the base member 10 and the second member 30 is adjusted. On the other hand, the first member 20 may have any structure as long as the distance between the base member 10 and the second member 30 can be adjusted.

For example, in a driving apparatus 1a of the first modified example shown in FIG. 10, a part of a first member 20a is extendably formed by a bellows-shaped member. According to the configuration, the distance between the base member 10 and the second member 30 may be adjusted like the above described embodiment.

Further, in a driving apparatus 1b of the second modified example shown in FIG. 11, a part of a first member 20b is bendably formed. According to the configuration, the distance between the base member 10 and the second member 30 may be adjusted like the above described embodiment.

Third and Fourth Modified Examples

Figure 12:
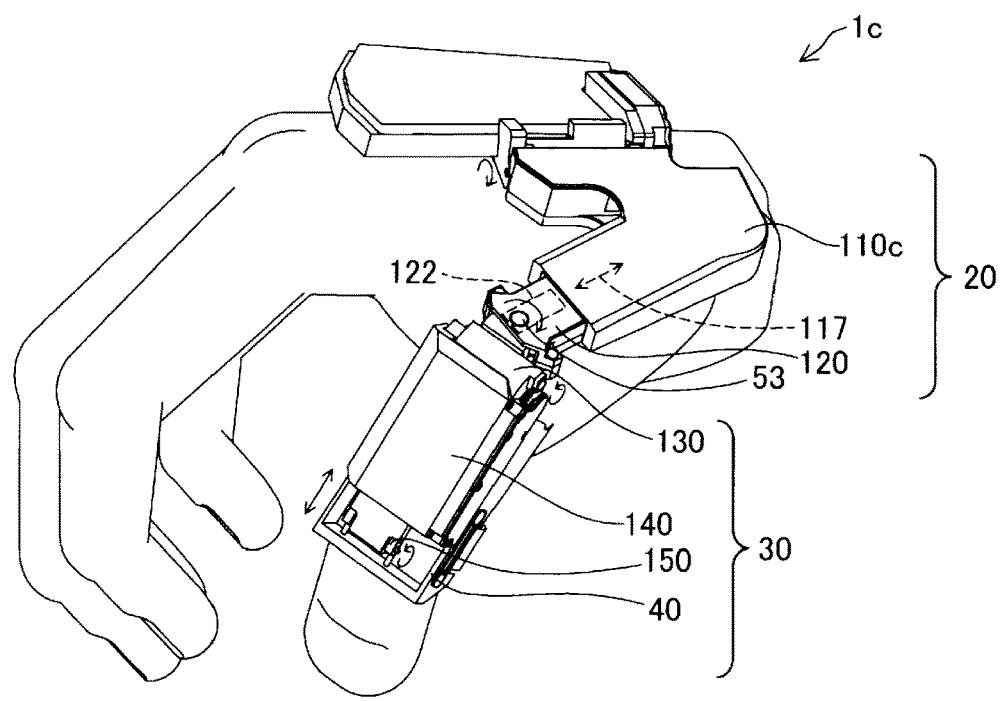
FIG. 12 shows a third modified example of the driving apparatus.
Figure 13:
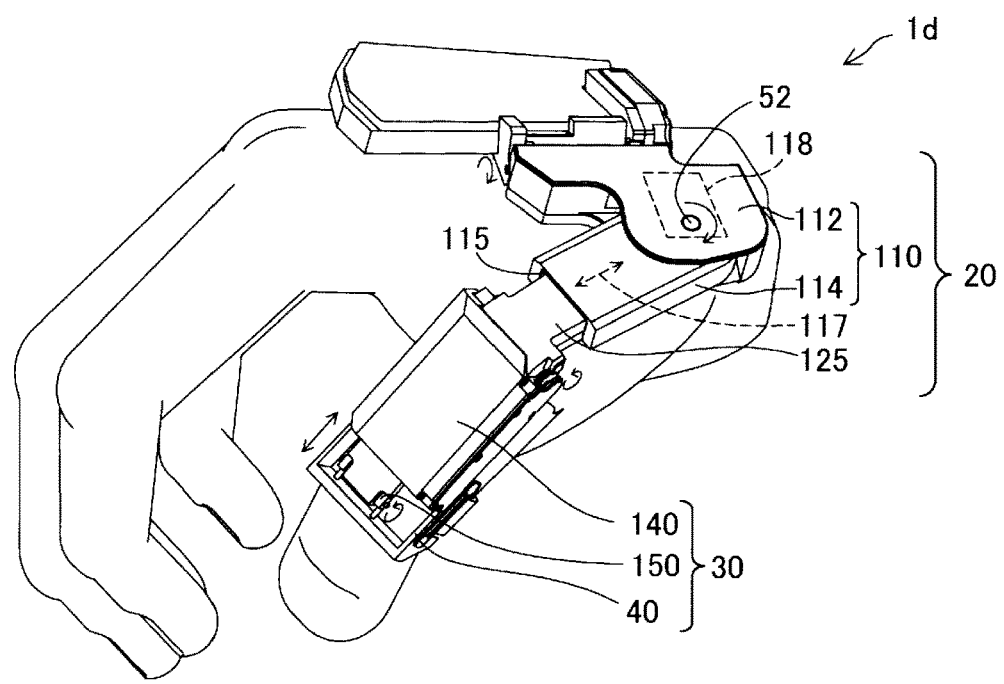
FIG. 13 shows a fourth modified example of the driving apparatus.

FIG. 12 shows a third modified example of the driving apparatus. FIG. 13 shows a fourth modified example of the driving apparatus. The driving apparatus 1 of the above described embodiment includes the second rotation shaft 52 and the third rotation shaft 53. However, one of these shafts (preferably, the second rotation shaft 52) may be omitted.

For example, in a driving apparatus 1c of the third modified example shown in FIG. 12, the second rotation shaft 52 is omitted. Accordingly, the second rotation unit 118 is also omitted and further the first auxiliary member 112 and the second auxiliary member 114 are integrated, and thereby, one first connecting part 110c is formed. Further, in a driving apparatus 1d of the fourth modified example shown in FIG. 13, the third rotation shaft 53 is omitted. Accordingly, the third rotation unit 122 is also omitted, and further, a connecting part 125 in which the second connecting part and the third connecting part are integrated is formed.

As shown in these drawings, even when one of the second rotation shaft 52 and the third rotation shaft 53 is omitted, the range of movement of the omitted shaft may be absorbed by play of the respective movable members. Further, as shown in FIGS. 12 and 13, as the number of rotation shafts is made smaller, the number of rotation units may be made smaller by the number, and downsizing, lightweight, and power saving of the driving apparatus 1 may be realized.

Fifth Modified Example

Figure 14:
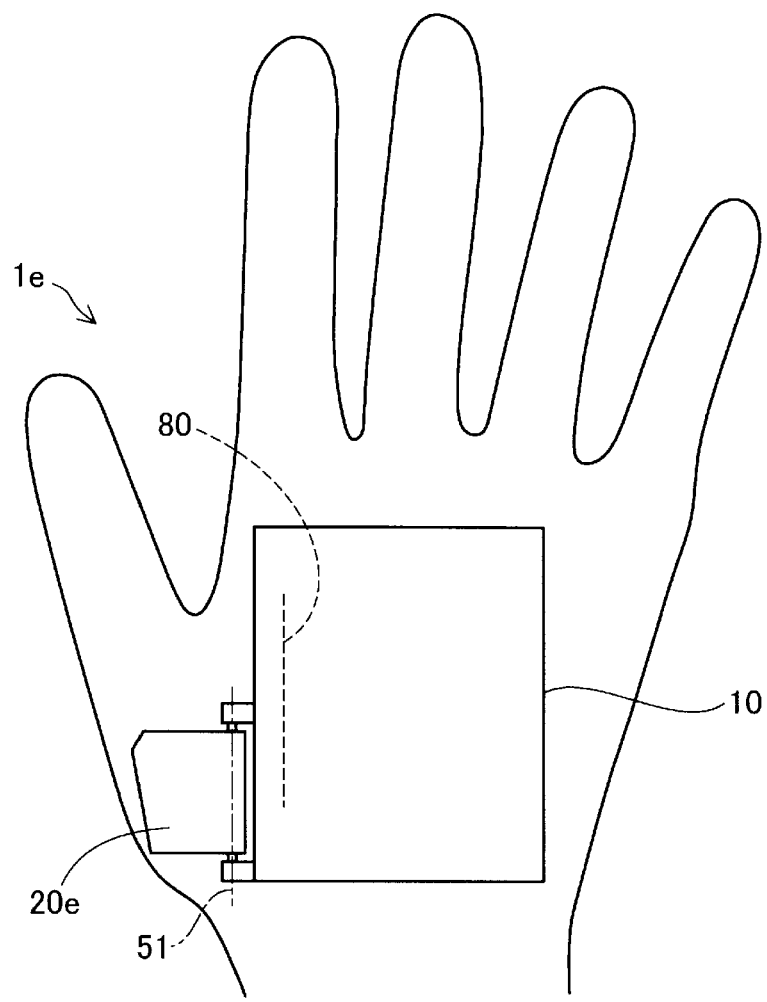
FIG. 14 shows a fifth modified example of the driving apparatus.

FIG. 14 shows a fifth modified example of the driving apparatus. The driving apparatus 1 of the above described embodiment includes the first member 20 and the second member 30, however, as shown in FIG. 14, the second member 30 may be omitted. In this case, a first member 20e does not necessarily include the second auxiliary member 114.

According to the configuration, a driving apparatus 1e having a single function that assists rotation of the thumb about the axis along the index finger metacarpal bone 80 may be provided.

Sixth Embodiment

In the above described embodiment, the first rotation unit 12 that drives the first rotation shaft 51 is provided on the base member 10, however, the first rotation unit 12 may be provided in the first member 20. Further, in the above described embodiment, the second rotation unit 118 that drives the second rotation shaft 52 is provided in the first auxiliary member 112, however, the second rotation unit 118 may be provided in the second auxiliary member 114. Furthermore, in the above described embodiment, the third rotation unit 122 that drives the third rotation shaft 53 is provided in the second connecting part 120, however, the third rotation unit 122 may be provided in the third connecting part 130. Moreover, in the above described embodiment, the fourth rotation unit 142 that drives the fourth rotation shaft 54 is provided in the fourth connecting part 140, however, the fourth rotation unit 142 may be provided in the third connecting part 130.

Seventh Modified Example

In the above described embodiment, as shown in FIGS. 2 and 3, the respective rotation shafts are driven by the rotation units using the piezoelectric bodies 651, however, the respective rotation shafts may be driven by various actuators. For example, as the actuators that drive the respective rotation shafts, general small motors, electromagnetic actuators, or the like can be used. Further, actuators including wires and tensioners that change tension of the wires, actuators including hoses and pumps that change oil pressure or air pressure within the hoses, or the like can be used.

Eighth Modified Example

The flat wiring member 70 in the above described embodiment may be provided, not limited in the joint mechanism 90 provided in the driving apparatus 1, but provided in any other joint mechanism. Further, the joint mechanism in which the flat wiring member 70 is inserted may include the actuator such as a rotation unit or not. Further, in the driving apparatus 1, not limited to the flat wiring member 70, but wiring may be provided by a wiring member having another form. For example, wiring may be provided by a general covered wire or a cable collecting a plurality of covered wires with a sheath.

Ninth Modified Example

In the above described embodiment, the driving apparatus 1 includes the first rotation unit 12, the second rotation unit 118, the third rotation unit 122, and the fourth rotation unit 142 as the rotation units, however, not all of the rotation units are necessarily provided. For example, the rotation unit for driving the joint without the need of motion assist can be omitted.

Tenth Modified Example

In the above described embodiment, it is assumed that the driving apparatus 1 is attached to the thumb of the human hand, however, the driving apparatus 1 may be used for application of assisting motions of joints not only of humans but also joints of living bodies including animals and joints of non-living bodies including robots.

The invention is not limited to the above described embodiment and modified examples, but may be realized in various configurations without departing from the scope of the invention. For example, in order to solve part or all of the above described problems or achieve part or all of the above described advantages, replacements and combinations can be appropriately made to the technical features in the embodiment and the modified examples corresponding to the technical features in the respective configurations described in Summary. Further, the technical features can be appropriately deleted unless the technical features are explained as essentials in the specification.

The entire disclosures of Japanese Patent Application Nos. 2014-185853, filed Sep. 12, 2014, 2014-185854, filed Sep. 12, 2014 and 2014-185856, filed Sep. 12, 2014 are expressly incorporated by reference herein.

What is claimed is:

1. A driving apparatus comprising:
   a base member;
   a first member rotatably provided on the base member; and
   a driver configured to rotate the first member around a rotation shaft, the driver being configured with:
      a vibrating plate including a piezoelectric body; and
      a driven member contacting with the vibrating plate, the driven member being configured to be driven in contact with the vibrating plate,
   wherein the first member is rotatable around the rotation shaft, the rotation shaft configured to be placed along an index finger metacarpal bone of a hand when the base member is placed on a back of the hand.

2. The driving apparatus according to claim 1, wherein a projection is provided on an end of the vibrating plate, and
   the projection abuts the driven member.

3. The driving apparatus according to claim 1, further comprising:
   an elastic member provided between the first member and the hand.

4. A driving method for a driving apparatus, the driving apparatus including:
   a base member;
   a first member rotatably provided on the base member; and
   a driver configured to rotate the first member around a rotation shaft, the driver being configured with:
      a vibrating plate including a piezoelectric body; and
      a driven member contacting with the vibrating plate, the driven member being configured to be driven in contact with the vibrating plate, the driving method comprising:
   placing the base member on a back of a hand; and
   rotating the first member around the rotation shaft, the rotation shaft configured to be placed along an index finger metacarpal bone of the hand.

5. The driving method according to claim 4, wherein a projection is provided on an end of the vibrating plate, and
   the projection abuts the driven member.

6. The driving method according to claim 4, further comprising:
   providing an elastic member between the first member and the hand.

* * * * *